United States Patent
Richter et al.

(10) Patent No.: US 6,564,647 B1
(45) Date of Patent: May 20, 2003

(54) METHOD FOR TESTING CERAMIC SOCKET INSERTS OF HIP JOINT ENDOPROSTHESES

(75) Inventors: Herbert Richter, Kongen (DE); Martin Wimmer, Fellbach (DE)

(73) Assignee: Ceramtec AG Innovative Ceramic Engineering, Plochingen (DE)

(*) Notice: Subject to any disclaimer, the term of this patent is extended or adjusted under 35 U.S.C. 154(b) by 0 days.

(21) Appl. No.: 09/786,909

(22) PCT Filed: Sep. 7, 1999

(86) PCT No.: PCT/EP99/06559

§ 371 (c)(1), (2), (4) Date: Jul. 11, 2001

(87) PCT Pub. No.: WO00/16066

PCT Pub. Date: Mar. 23, 2000

(30) Foreign Application Priority Data

Sep. 12, 1998 (DE) .......................... 198 41 826

(51) Int. Cl.$^7$ ................................................ G01N 3/08
(52) U.S. Cl. .......................................... 73/818; 623/22
(58) Field of Search ........................ 73/818, 823, 824, 73/825, 856, 379.08; 623/22

(56) References Cited

U.S. PATENT DOCUMENTS 5,549,693 A * 8/1996 Roux et al. ............... 623/22.14
6,049,976 A * 4/2000 Khandros ................. 228/180.5
6,176,140 B1 * 1/2001 Autenrieth et al. ......... 623/908

FOREIGN PATENT DOCUMENTS

| DE | 2036284 | 3/1971 |
| DE | 2728007 | 8/1978 |
| DE | 4411508 | 10/1995 |
| DE | 19718615 | 1/1998 |

* cited by examiner

Primary Examiner—M. Noori
(74) Attorney, Agent, or Firm—Antonelli, Terry, Stout & Kraus, LLP

(57) ABSTRACT

A method tests a ceramic socket insert of a hip joint endoprosthesis in which, in use, a spherical head articulates against a functional inner surface of a ceramic socket insert which is anchored in a pelvic bone by means of a socket housing. The method includes providing the ceramic socket insert in a holding arrangement, applying a predetermined pressing force to a predetermined sub-area of the functional inner surface of the ceramic socket insert, and applying a supporting force to a sub-area of an outer surface of the ceramic socket insert to counteract the pressing force. The predetermined sub-area of the functional inner surface symmetrically surrounds a pole of the inner surface of a ceramic socket insert. The predetermined force is such that stresses generated in the ceramic socket insert are higher than stresses generated in the case of a physiological load.

13 Claims, 2 Drawing Sheets

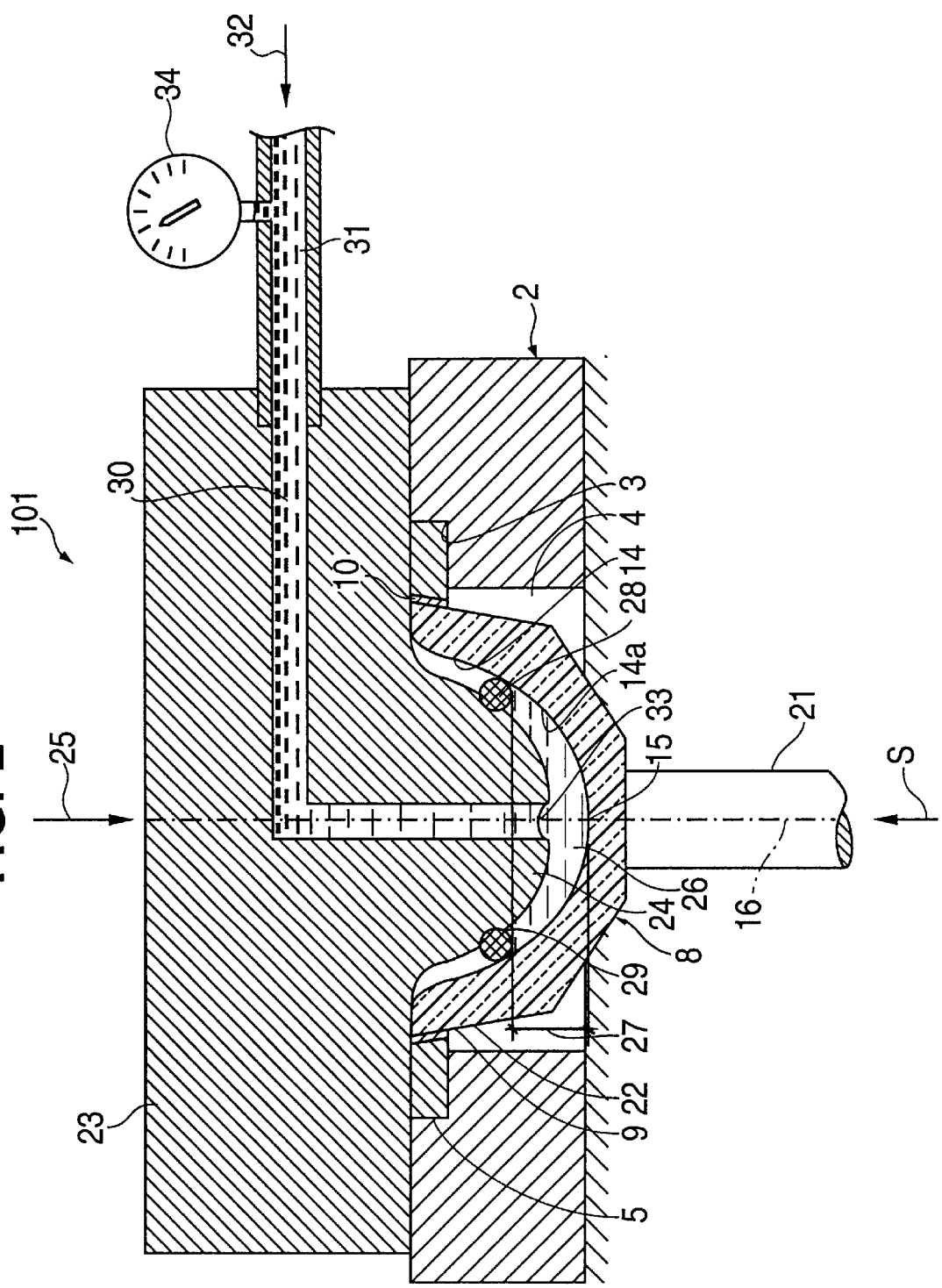

METHOD FOR TESTING CERAMIC SOCKET INSERTS OF HIP JOINT ENDOPROSTHESES

BACKGROUND OF THE INVENTION

The invention relates to a method for testing ceramic socket inserts of hip-joint endoprostheses.

Currently, hip-joint endoprostheses consist, as a rule, of modularly constructed systems. A metal shaft with a pin, on which a spherical head is placed, is anchored in the femur. The spherical head articulates against a socket or a socket insert. A socket is implanted directly in the femur, whilst a socket insert is first inserted in a socket housing which is then anchored in the pelvic bone.

In addition to components for endoprostheses of the hip joint made of metal and plastics material, there are also components that are made of high-purity, high-density ceramic material. These components, present significant advantages, in contrast to components made of different materials, such as complete biocompatibility and maximum wear resistance. Doubts exist, however, regarding the mechanical strength of such components, since ceramic materials are brittle, which means that instances of non-homogeneity of the material, for example micro-cracks, represent an increased risk of fracture in the event of loading. The reliability against defects resulting from components that are risk-attendant can be increased if these components are successfully detected and eliminated out by means of a suitable test after they have been produced. It is not, however, possible to detect components that are risk-attendant with any certainty by means of the usual non-destructive testing methods, for example X-ray testing, ultrasonic testing or dye-penetration methods.

For these reasons, method have been developed with which it is possible to test, in particular, components of hip-joint endoprostheses that are made of ceramic materials. For example, a method for testing ceramic sockets or socket inserts of hip-joint endoprostheses is known from DE 197 18 615 A1, in which a force is allowed to act on the inner surface of the latter in such a way that all the volume elements of the socket or socket insert respectively that are under a load, when physiologically loaded, become loaded and stresses are generated thereby that are higher, by a defined factor, than the stresses that are generated in the case of the physiological load.

In the case of the known overload tests, the so-called proof tests, carried out on ceramic socket inserts, the difficulty lies in generating the same stress ratios during the test that prevail in the case of a socket insert that is inserted in a socket housing, which in turn is implanted in a hip joint, and is loaded with a spherical head.

It is not possible to insert the socket inserts into the socket housings for testing purposes in order to be able to carry out a proof test as a quality control after production. After testing, it would be impossible to remove the socket inserts from the respective socket housing again without damage. Moreover, on account of the manufacturing tolerances of socket inserts and socket housings, reproducibility of the contact ratios between the components would not be guaranteed. This is necessary, however, since in a proof test it must be possible to repeat the most unfavourable case of stress distribution caused by the contact of the components.

SUMMARY OF THE INVENTION

The object of the present invention is therefore to propose a testing method with which a distribution of stresses is attained in the socket inserts comparable to those stresses that occur in loaded socket inserts which are inserted into a socket housing which in turn is implanted in the pelvic bone.

The object is achieved by introducing the testing force into the socket insert by way of a predetermined sub-area of the functional surface, which symmetrically surrounds the pole of the inner functional surface of the socket insert, and by applying a supporting force that counteracts the testing force simultaneously to a sub-region of the outer surface of the socket insert.

In the testing method in accordance with the invention, a supporting force acts on a sub-region of the outer surface of the spherical cap-shaped socket insert at the same time as the action of the testing force. During testing, the supporting force is increased as the loading by the testing force increases. The testing force is introduced by way of a predetermined sub-area of the inner surface of the socket insert, the inner spherical cap, which symmetrically surrounds the pole of the socket insert. As a result, stresses are generated in the socket insert in the same way as stresses also occur in an actual case of loading in the socket insert. The whole outer surface of the socket insert with conically shaped regions is displaced during testing under sufficiently uniform tensile strain.

The size of the sub-area of the functional surface of the socket insert, upon which the testing force acts, is predetermined by the height of the section which is covered by the sub-area. The height of the section is to amount to approximately 15% to 30% of the maximum inside diameter of the functional surface of the socket insert. Such is the height of a spherical section that goes right into the socket insert and by way of which the testing force is mechanically introduced into the socket insert by means of a die or the space in which the testing force is applied by means of a pressure fluid under pressure that, as a result of the predetermined height of the section, a loaded area is created that renders possible optimum simulation of the actual loading of a socket insert.

The testing force increases linearly up to a predetermined maximum value which is to be attained within approximately 10 seconds. Like the testing force, the supporting force likewise increases linearly and amounts to approximately 10% of the testing force. The testing force is introduced perpendicularly in the direction of the pole of the functional area. The supporting force is introduced in the opposite direction. To this end, for example, a die can press against the outer surface of the socket insert, with it being possible to generate the supporting force hydraulically, pneumatically or with springs.

It is advantageous to use, as a basis in each case, the maximum diameter of the functional areas of the socket inserts as a criterion for the level of the testing forces. For example, in the case of a socket insert having a maximum diameter of the functional area of 28 mm and a service life of 20 years that is to be guaranteed, a testing force of 13 to 15 kN is selected.

If the testing force is introduced mechanically by means of a spherical section that is arranged at the end of the die, the material of this section is not to damage the functional surface of the socket insert during testing. Moreover, it must be guaranteed that manufacturing tolerances are compensated for. For this reason, it is advantageous if at least one surface layer of the section consists of a material that is softer than the material of the socket insert and has a module of elasticity of approximately 300 to 1500 MPa. Plastics materials, in particular polytetrafluoroethylene, have proved to be suitable.

The socket inserts are held in the holding support of the testing device in accordance with the invention in a so-called receiving ring. The receiving ring supports the socket inserts in the edge region of the maximum outer periphery. The wall of the opening of the receiving ring extends, so as to be adapted to this wall region, in a conical manner. Whilst the outside diameters of the receiving rings are constant, the diameters of the receiving openings can be different in accordance with the outside diameters of the socket inserts. As a result, advantageously it is possible to be able to test socket inserts with different diameters of the functional areas in one and the same receiving arrangement, merely by changing the receiving rings.

In a further advantageous development of the invention, is a narrow ring made of a ductile material laid between the receiving ring and the socket insert. The ring can, for example, be made of copper or another soft metal or even of a suitable plastics material. With the aid of this ring of ductile material it is possible to reconcile manufacturing tolerances and compensate for possible structures, for example surface roughness. Furthermore, when the testing force is acting, friction-associated, uneven jamming and tilting of a socket insert inside the receiving ring are avoided. The withdrawal of a socket insert out of the receiving ring and the subsequent removal of the ring of ductile material are possible without a tool and thus without the risk of damage to the socket insert.

BRIEF DESCRIPTION OF THE DRAWINGS

The method in accordance with the invention is explained in greater detail with the aid of diagrammatic representations of two embodiments of the testing devices. In the drawings:

FIG. 2 shows a section through a testing device in which the testing force is generated hydraulically.

DETAILED DESCRIPTION OF THE DRAWINGS

Figure 1:
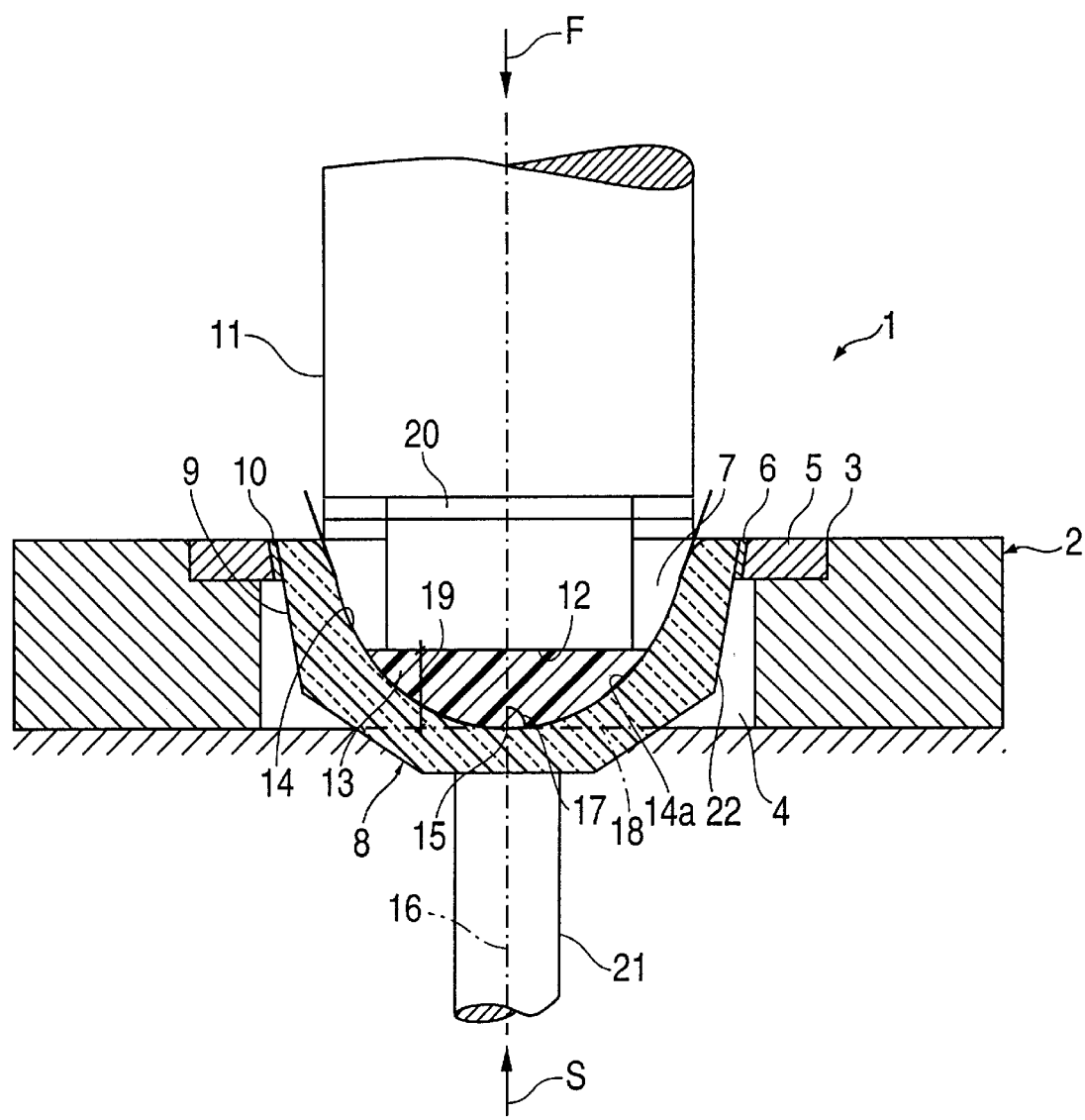
FIG. 1 shows a section through a testing arrangement with a mechanical testing die.

In FIG. 1 a testing arrangement 1 for mechanically applying the testing force F is denoted by 1. Resting in a frame, which is not shown here in greater detail, is the holding arrangement 2 with a circular recess 3 which surrounds an opening 4. A receiving ring 5 which preferably consists of a high-strength material is inserted in the circular recess 3. The wall 6 of the opening 7 for receiving a socket insert 8 extends conically. It is adapted to the edge region 9 of the spherical cap-shaped socket inserts 8. The diameter of the opening 7 and also the conical character of the wall 6 are provided for socket inserts that have the same maximum diameter of functional area. Other receiving rings with suitable openings are available for socket inserts that have different functional surface diameters.

In the edge region 9, the socket insert 8 is suspended in the opening 4 of the receiving ring 5. A ring 10 that is made of a ductile material is located between the edge region 9 of the socket insert 8 and the wall 6 of the receiving ring 5. For example, this is a ring made of copper sheet and has a height substantially equal to the thickness of the receiving ring 5. On account of the ductility of the material, manufacturing tolerances and possible structures in the edge region 9 of the socket insert 8 are compensated for. Moreover, the removal of the socket insert 8 from the receiving ring 5 is facilitated.

The testing force F is applied by means of a die 11. The die 11 can carry a spherical section 13 on its end face 12, the radius of which end face is adapted to the functional area 14 of the socket insert 8. The spherical section 13, as an exchangeable portion, can, however, also be laid loosely on the functional area 14 of the socket insert 8. The spherical section 13 covers the sub-area 14a, by way of which the testing force is introduced into the socket insert 8. In the present exemplifying embodiment, the material of the spherical section 13 is polytetrafluoroethylene having a modulus of elasticity of approximately 450 MPa. The material endures the high pressing forces which are brought about by the testing force and leaves behind no traces on the highly sensitive functional area 14.

The pole of the section 13 and the pole of the inner spherical cap, the functional area 14, coincide at point 15. The central line 16 of the die 11 stands at a right angle 17 to a tangent 18 at the pole 15. The testing force F is introduced into the socket insert 8 by means of the die 11 in the direction of the central line 16. The height 19 of the section 13 is determined by the maximum diameter 20 of the functional area 14 and can amount to 15 to 30% thereof.

The operating direction of the supporting force S likewise extends through the pole 15, perpendicularly to the tangent 18. The supporting force S is applied by means of a die 21 which is placed upon the outer surface 22 of the socket insert 8 symmetrically in relation to the central line 16 below the pole 15. As a result of the application of a supporting force S in accordance with the invention, the whole outer surface of the socket insert with conically shaped regions is displaced under tensile stress during the testing in a sufficiently uniform manner. This is advantageous because on account of the possible manufacturing tolerances of the conically shaped area of the socket housing for receiving the socket insert it is not possible to foresee on which region of the outer surface of the socket insert, a load will be concentrated on account of tensile stresses during actual use as an implant. If, on account of a testing force F that is applied, fracture of a socket insert results, the shape and position of the fragments correspond to a fracture which results when a socket insert that has been inserted in an implanted socket housing is overloaded.

A further embodiment of the testing arrangement is shown in FIG. 2, in which the testing force is applied hydraulically by means of a fluid which is under pressure. The holding arrangement and the socket insert have the same structure as in the previous exemplifying embodiment. Corresponding features are therefore denoted by the same reference symbols.

Instead of a die, which acts on the socket insert with a testing force, a metal block 23 is placed upon the holding arrangement 2. Its contour, which faces the functional area 14 of the socket insert 8, is adapted corresponds to a spherical section 24 placed upon the metal block 22. A force 25 acts upon the metal block 23 in a uniform manner, which force 25 is greater than the testing force applied by the pressure fluid 31 so that, during testing, the metal block 23 does not lift off from the holding arrangement 2.

A gap 26 exists between the spherical section 24 and the functional area 14. It is the space which is tilled with pressure fluid 31. The size of the sub-area 14a is predetermined by the height 27 of the space, by the predetermined distance 27 from the pole 15, at which the gap 26 is sealed by an annular sealing element 28. In this connection, the annular sealing element 28 lies in an annular recess 29 of the spherical section 24 in such a way that, when the block 23 is laid upon the holding arrangement 2 before the testing is initiated, no force is exerted on the socket insert 8. It is only when the pressure fluid is pumped in that the sealing elements 28 close off the gap 26. The sub-area 14a which is closed off by the sealing element 28 is the area by way of which the testing force is introduced into the socket insert 8 by means of the pressure fluid 31.

The block 23 has bores 30 as a feed line for the pressure fluid 31. The pressure fluid 31 is pumped by a pump, which is not shows here, in the direction of the arrow 32 through the outlet opening 33 into the gap 26 between the spherical section 24 and the functional surface 14 of the socket insert 8.

The pressure characteristic and the pressure achieved in the pressure fluid 31, and thus the testing force that is applied, can be checked by means of a pressure-measuring instrument 34 that is indicated. Any media measuring instrument 34 that is indicated. Any media that do not act on and also do not contaminate the surfaces of the ceramic socket inserts are suitable as pressure fluids.

During testing, the maximum testing force is to be attained within approximately 10 seconds and removal of the load is to be achieved in less than 0.5 seconds. As a result, any possible extension of micro-cracks that are formed is to be prevented.

Socket inserts that have stress-concentrating material inhomogeneities that are to be regarded as critical do not pass this test and are destroyed. However, those sockets that have passed the test show a level of strength that is higher than the limits defined by the overload test.

What is claimed is:

1. A method for testing a ceramic socket insert of a hip joint endoprosthesis in which, in use, a spherical head articulates against a functional inner surface of a ceramic socket insert which is anchored in a pelvic bone by means of a socket housing, the method comprising:

providing the ceramic socket insert in a holding arrangement;

applying a predetermined pressing force to a predetermined sub-area of the functional inner surface of the ceramic socket insert, the predetermined sub-area symmetrically surrounding a pole of the inner surface of a ceramic socket insert, the predetermined force being such that stresses generated in the ceramic socket insert are higher than stresses generated in the case of a physiological load; and applying a supporting force to a sub-area of an outer surface of the ceramic socket insert to counteract the pressing force.

2. Method according to claim 1, wherein a size of the sub-area, upon which the predetermined pressing force acts, is predetermined by the choice of the height of a section covered by the functional area of the ceramic socket insert.

3. Method according to claim 1, wherein a height of the section is approximately 15% to 30% of the maximum diameter of the functional inner surface of the ceramic socket insert.

4. Method according to claim 1, wherein the pressing force increases linearly up to the predetermined maximum value, and in that the supporting force likewise increases linearly.

5. Method according to claim 1, wherein the supporting force is approximately 10% of the testing force.

6. Method according to claim 1, wherein a level of the predetermined pressing force is predetermined as a function of a maximum diameter of the functional inner surface of the ceramic socket insert.

7. Method according to claim 1, wherein the predetermined pressing force is determined taking into consideration a period of use of the socket insert as an implant.

8. Method according to claim 1, wherein the predetermined pressing force is applied mechanically by a spherical section that goes right into the ceramic socket insert, the spherical section having a radius which corresponds to a radius of the functional inner surface of the ceramic socket insert and a height which amounts to a predetermined height of the section over the surface of which the predetermined pressing force is to be introduced into the ceramic socket insert.

9. Method according to claim 8, wherein at least a surface of the spherical section that acts upon the functional inner surface of the ceramic socket insert in order to introduce the predetermined pressing force is coated with a material that has a modulus of elasticity of approximately 300 to 1500 Mpa.

10. Method according to claim 9, wherein the material that has a modulus of elasticity of approximately 300 to 1500 Mpa is polytetrafluoroethylene.

11. Method according to claim 1, wherein the predetermined pressing force is applied hydraulically, and a size of the sub-area of the functional inner surface of the ceramic socket insert is predetermined by a height of a space that is covered by the functional inner surface and which is filled with a pressure fluid.

12. Method according to claim 1, herein the ceramic socket inserts are supported in the holding arrangement by receiving rings, the receiving rings having receiving openings which are matched to an outside diameter of the ceramic socket insert, wherein the ceramic socket insert is held in an edge region of its maximum outer periphery.

13. Method according to claim 12, wherein a narrow ring made of a ductile material is laid between the receiving ring and the ceramic socket insert.

* * * * *